(12) United States Patent
Stanton et al.

(10) Patent No.: US 9,976,660 B2
(45) Date of Patent: May 22, 2018

(54) HIGH PRESSURE DOME CHECK VALVE

(71) Applicant: Halkey-Roberts Corporation, St. Petersburg, FL (US)

(72) Inventors: Katherine J. Stanton, St. Petersburg, FL (US); Stephen P. Bello, Clearwater, FL (US)

(73) Assignee: Halkey-Roberts Corporation, St. Petersburg, FL (US)

(*) Notice: Subject to any disclaimer, the term of this patent is extended or adjusted under 35 U.S.C. 154(b) by 0 days. days.

(21) Appl. No.: 15/138,015

(22) Filed: Apr. 25, 2016

(65) Prior Publication Data

US 2016/0312910 A1    Oct. 27, 2016

Related U.S. Application Data

(60) Provisional application No. 62/151,497, filed on Apr. 23, 2015.

(51) Int. Cl.
   *F16K 15/14*    (2006.01)
   *A61M 39/24*    (2006.01)
   *A61M 39/26*    (2006.01)

(52) U.S. Cl.
   CPC .......... *F16K 15/141* (2013.01); *A61M 39/24* (2013.01); *A61M 39/26* (2013.01); *F16K 15/144* (2013.01);
   (Continued)

(58) Field of Classification Search
   CPC .... F16K 15/141; F16K 15/144; F16K 15/145; F16K 15/147; A61M 39/24; A61M 39/26;
   (Continued)

(56) References Cited

U.S. PATENT DOCUMENTS

| | | | |
|---|---|---|---|
| 3,831,629 A | 8/1974 | Mackal et al. | |
| 4,369,812 A | 1/1983 | Paradis et al. | |
| 4,499,916 A | 2/1985 | Hanson et al. | |
| 5,349,984 A | 9/1994 | Weinheimer et al. | |
| 5,573,516 A | 11/1996 | Tyner | |
| 5,746,414 A | 5/1998 | Weldon et al. | |
| 5,899,624 A * | 5/1999 | Thompson ........... | B43K 5/1845 401/196 |

(Continued)

FOREIGN PATENT DOCUMENTS

| | | | |
|---|---|---|---|
| WO | WO 9739791 A1 * | 10/1997 | ................ A61J 1/18 |
| WO | WO 2009144599 A1 * | 12/2009 | ........ A61M 5/16804 |

(Continued)

*Primary Examiner* — Mary McManmon
*Assistant Examiner* — Hailey K Do
(74) *Attorney, Agent, or Firm* — GrayRobinson, P.A.

(57) ABSTRACT

A check valve including an elastomeric valve element having a dome-shaped configuration that seals in its at-rest position occluding fluid flow in both directions. The dome-shaped elastomeric valve element is constructed in such a way to be deflectable, such as being activated by the external device such as a male luer whereupon the valve is cracked open to become a two-way valve allowing flow in both directions. The valve element may also be cracked open by sufficient fluid pressure in its inlet. The valve element is self-aligning. The dome-shaped of the valve element includes cut-outs for additional fluid flow, thereby streamlining flow while reducing the potential for air entrapment. The underside of the dome-shaped valve element also includes a thickened concave undersurface and thickened support legs to significantly increase the resistance to high backpressures, while also minimizing potential air entrapment.

11 Claims, 8 Drawing Sheets

(52) U.S. Cl.
CPC .......... *F16K 15/145* (2013.01); *F16K 15/147* (2013.01); *A61M 2039/242* (2013.01); *A61M 2039/246* (2013.01); *A61M 2039/2406* (2013.01); *A61M 2039/2433* (2013.01); *A61M 2039/2446* (2013.01); *A61M 2039/2493* (2013.01); *Y10T 137/784* (2015.04); *Y10T 137/7895* (2015.04)

(58) Field of Classification Search
CPC .. A61M 2039/2406; A61M 2039/2433; A61M 2039/2446; A61M 2039/246; A61M 2039/242; A61M 2039/2493; Y10T 137/7895; Y10T 137/784
See application file for complete search history.

(56) References Cited

U.S. PATENT DOCUMENTS

| | | | |
|---|---|---|---|
| 5,909,747 A * | 6/1999 | Schieber | F16K 7/17 137/492 |
| 5,992,462 A | 11/1999 | Atkinson et al. | |
| 6,390,120 B1 | 5/2002 | Guala | |
| 7,296,782 B2 | 11/2007 | Enerson et al. | |
| 7,306,197 B2 * | 12/2007 | Parrino | A61M 39/26 251/149.6 |
| 7,641,174 B2 | 1/2010 | Enerson et al. | |

FOREIGN PATENT DOCUMENTS

| | | | |
|---|---|---|---|
| WO | WO 2012175412 A1 * | 12/2012 | A61N 39/26 |
| WO | WO 2013116670 A1 * | 8/2013 | A61M 39/26 |

* cited by examiner

HIGH PRESSURE DOME CHECK VALVE

CROSS-REFERENCE TO RELATED INVENTIONS

This application claims the benefit of provisional application No. 62/151,497, filed Apr. 23, 2015, the disclosure of which is hereby incorporated by reference herein.

BACKGROUND OF THE INVENTION

Field of the Invention

This invention relates to check valves, and relates more specifically to a check valve for medical usage.

Description of the Background Art

Presently, there are many types of check valves which are designed to control the one-way flow of a fluid therethrough. One common type of check valve comprises a valve element, such as a ball or spring biased valve stem, reciprocatingly positioned within a valve body providing a fluid passageway. The flow of fluid in one direction through the valve body is permitted upon displacement of the stem as it flows around the valve stem to exit the valve body. In the opposite direction, however, the fluid pressure along with the spring forces the valve stem against a valve seat, thereby inhibiting, or checking the flow of fluid therethrough. In this manner, this type of check valve effectively provides that fluid can flow only in one direction through the check valve. An example of this type of valve is found in U.S. Pat. No. 5,349,984, the disclosure of which is hereby incorporated by reference herein.

Check valves employing an elastomeric stem without the use of a spring are described in U.S. Pat. No. 3,831,629, the disclosure of which is hereby incorporated by reference herein. Other check valves employing umbrella or disk-like elastomeric elements are described in the following U.S. Pat. Nos. 5,992,462; 4,499,916 and 4,369,812, the disclosures of which are hereby incorporated by reference herein. Some check valves employ elastically deformable diaphragm-like elements as described in U.S. Pat. No. 6,390,120, the disclosure of which is hereby incorporated by reference herein. Another check valve employing conical or hollow elastomeric elements where fluid flow is arranged to pass through the element itself is described in U.S. Pat. Nos. 5,573,516 and 5,746,414, the disclosures of which are hereby incorporated by reference herein. Some of the designs described above allow for bi-directional fluid flow if accessed by the appropriate connector such as a luer fitting commonly used in the medical fluid delivery field.

More contemporary check valves are reflected in U.S. Pat. Nos. 7,296,782 and 7,641,174 entitled "Dome Check Valve", the disclosures of which are hereby incorporated by reference herein. The present invention represents an improvement over such dome check valves to increase the operation of the valve at high pressures.

Therefore, it is an object of this invention to provide an improvement which overcomes the aforementioned inadequacies of the prior art devices and provides an improvement which is a significant contribution to the advancement of the check valve art.

Another object of this invention is to provide a valve that seals itself to restrict fluid flow at very high back pressure on the order of about 1200 psi.

Another object of this invention is to provide a valve that includes a valve element made from a dome-like shaped elastomeric material which seals in its at-rest position occluding fluid flow in both directions.

Another object of this invention is to provide a valve including a dome-shaped elastomeric valve element that is constructed in such a way to be deflectable, such as being activated by the external device such as a male luer whereupon the valve is cracked open to become a two-way valve allowing flow in both directions.

Another object of this invention is to provide a valve having a valve element that is self-aligning.

Another object of this invention is to provide a valve having a valve element is self-supporting and when assembled in the valve, exerts a predetermined pressure against the valve seat thus sealing the valve, the valve element deflecting at the center after pressure rises over the cracking pressure or by being accessed by a syringe or other device, thus opening the bi-directional flow path.

Another object of this invention is to provide a valve having a dome-shaped valve element wherein the dome includes cut-outs for additional fluid flow, thereby streamlining flow while reducing the potential for air entrapment.

Another object of this invention is to provide a valve having a dome-shaped valve element having a thickened concave undersurface and thickened support legs to significantly increase the resistance to high backpressures, while also minimizing potential air entrapment that might otherwise occur underneath the prior art dome check valves noted above.

The foregoing has outlined some of the pertinent objects of the invention. These objects should be construed to be merely illustrative of some of the more prominent features and applications of the intended invention. Many other beneficial results can be attained by applying the disclosed invention in a different manner or modifying the invention within the scope of the disclosure. Accordingly, other objects and a fuller understanding of the invention may be had by referring to the summary of the invention and the detailed description of the preferred embodiment in addition to the scope of the invention defined by the claims taken in conjunction with the accompanying drawings.

SUMMARY OF THE INVENTION

For the purpose of summarizing the invention, this invention comprises a valve that seals itself to restrict fluid flow at very high back pressure on the order of about 1200 psi. The valve includes a valve element made from a dome-like shaped elastomeric material which seals in its at-rest position occluding fluid flow in both directions. The dome-shaped elastomeric valve element is constructed in such a way to be deflectable, such as being activated by the external device such as a male luer whereupon the valve is cracked open to become a two-way valve allowing flow in both directions. The valve element may also be cracked open by sufficient fluid pressure in its inlet. The valve element is self-aligning. The valve element is designed in such a way that various opening pressures are achievable by a simple modification of a mold tool, for example by changing a core pin.

The valve element of the valve is self-supporting and when assembled in the valve, exerts a predetermined pressure against the valve seat thus sealing the valve. The element deflects at the center after pressure rises over the predetermined cracking pressure or by being accessed by a syringe or other device, thus opening the bi-directional flow path.

Unlike the prior art dome check valves noted above, the dome of the valve element includes cut-outs for additional fluid flow, thereby streamlining flow while reducing the potential for air entrapment. The underside of the dome-shaped valve element also includes a thickened concave undersurface and thickened support legs to significantly increase the resistance to high backpressures, while also minimizing potential air entrapment that might otherwise occur underneath the prior art dome check valves noted above.

The valve housing is manufactured in a modular fashion, allowing the assembly of the same valve element into various housings having different connecting arrangements, such as ML, MLL, tubing fitment or barbed connector. The components are producible reliably by high cavitation molds and are suitable for high speed assembly process, thereby resulting in a highly economical valve. None of the valve components require registration radially during assembly.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENTS

Figure 1:
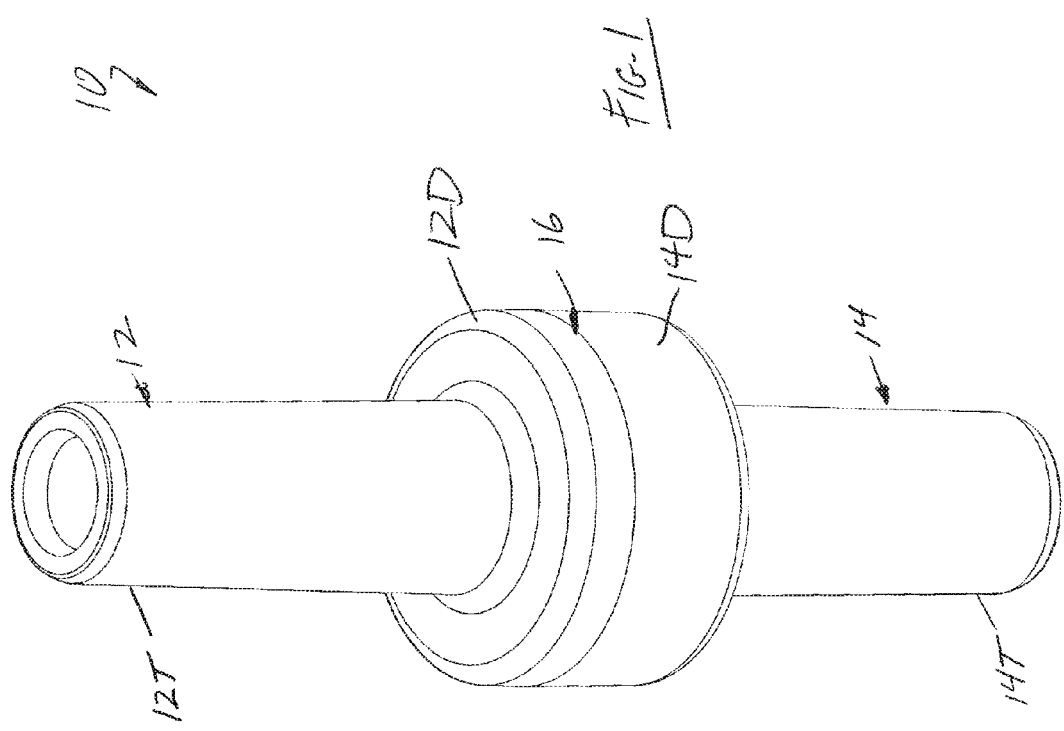
FIG. 1 is an enlarged isometric view of the valve of the invention having tubular inlet and outlet arrangements.

As best shown in FIG. 1, the valve 10 of the invention comprises inlet housing 12 and an outlet housing 14 fastened, preferably permanently, together at joint 16 such as by welding or bonding. The inlet and outlet housing 12 & 14 include tube fittings 12T and 14T respectively; however, it shall be appreciated that the housing 12 & 14 may include other types of fittings such as a luer lock fitting without departing from the spirit and scope of this invention. For example, one or both of the inlet and outlet housings 12 & 14 may be provided with barbed hose fittings, luer fittings or locking luer fitting (see the various embodiments in the Dome Check Valves of U.S. Pat. Nos. 7,296,782 and 7,641,174 cited above). Both the inlet and outlet housing 12 & 14 further include a generally dome-shaped larger diameter configuration 12D and 14D respectively, that are appropriately configured to mate together to then be fastened at joint 16.

Figure 2:
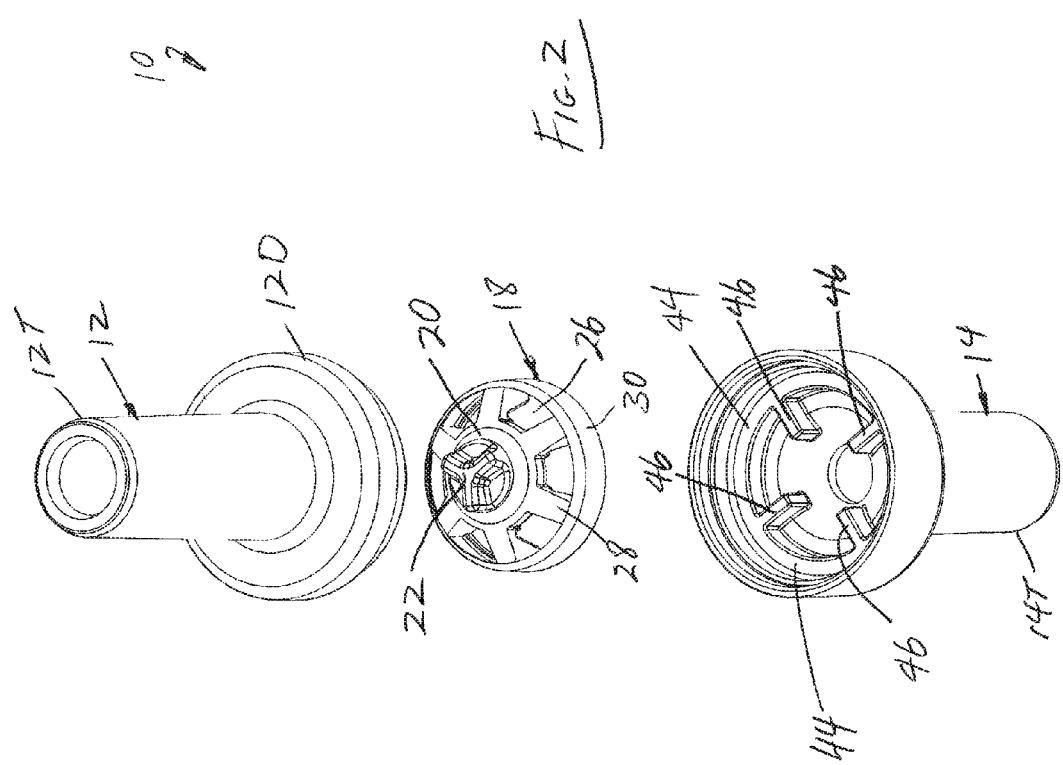
FIG. 2 is a top exploded view of FIG. 1 showing the inlet housing, the valve element and the outlet housing.
Figure 3:
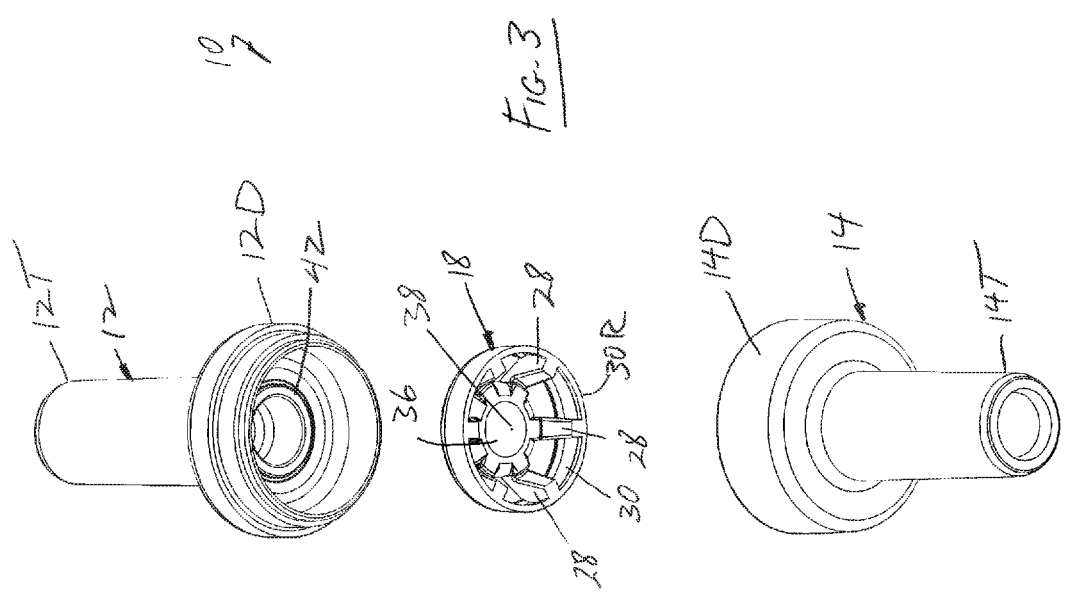
FIG. 3 is a bottom exploded view of FIG. 1 showing the inlet housing, the valve element and the outlet housing.
Figure 4:
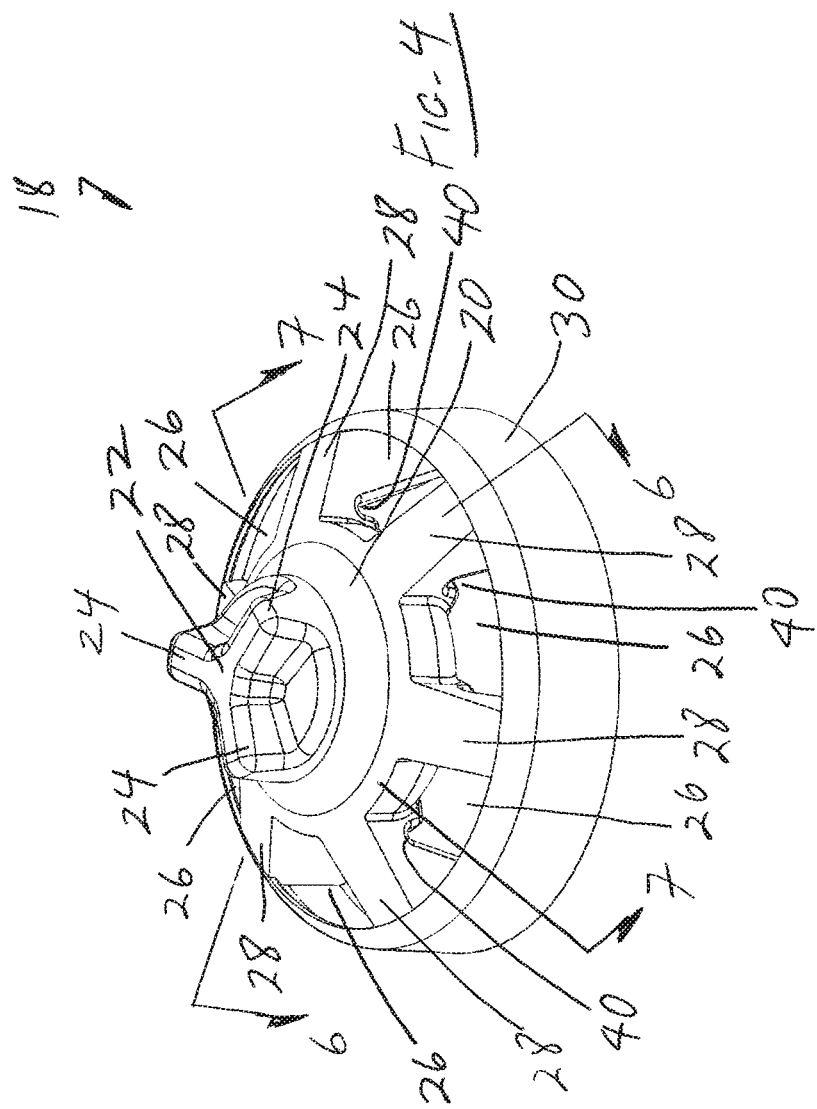
FIG. 4 is an enlarged top perspective view of the valve element.
Figure 5:
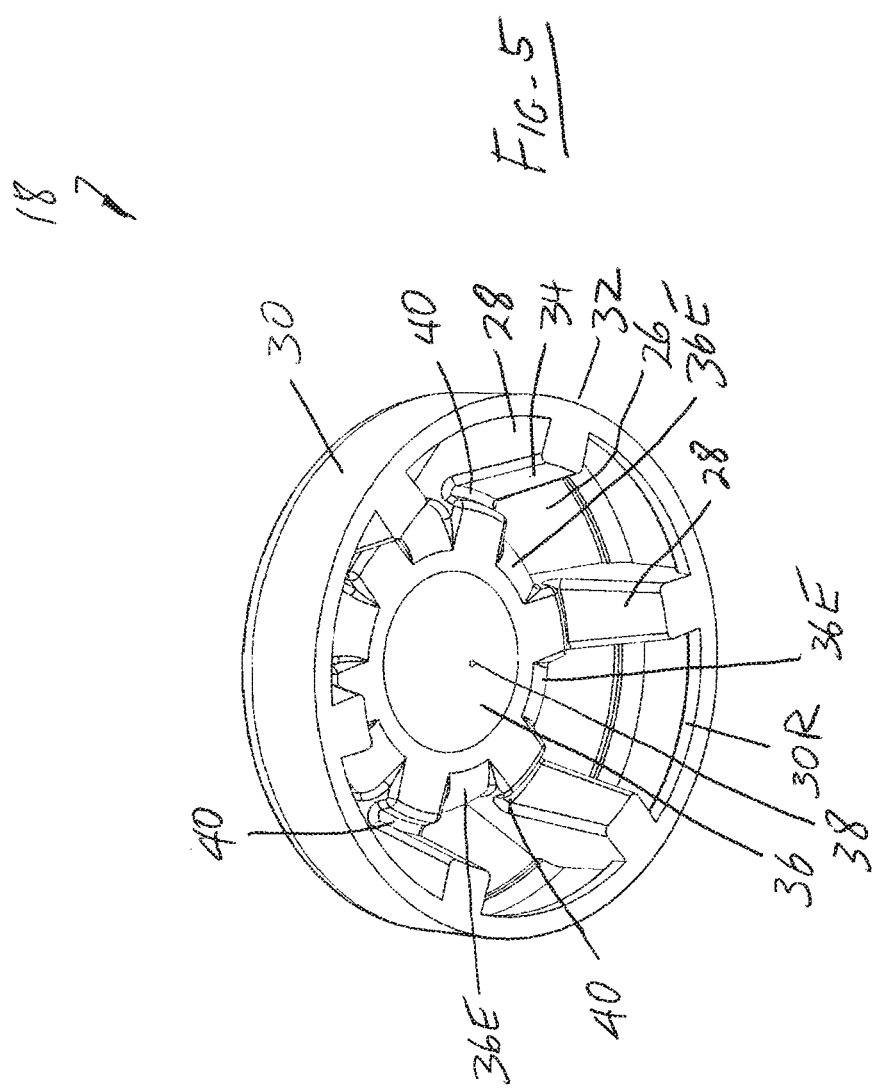
FIG. 5 is an enlarged bottom perspective view of the valve element.

As shown in FIGS. 2 and 3, an elastomeric dome-shaped valve element 18 is entrained between the dome-shaped larger diameter configurations 12D & 14D of the inlet and outlet housing 12 & 14.

As better shown in FIGS. 4-7, the valve element 18 comprises a generally dome-shaped configuration 20 with a central integral stem 22, preferably frustoconical, positioned concentrically therewith that extends into the inlet housing 12. The central integral stem 22 comprises a star-shaped configuration with a plurality of equally-spaced radial projections 24 (e.g., 3 are shown respectively positioned at 120 degrees) to allow fluid flow therearound in the event the stem 22 is engaged by the tip of a luer fitting such as a syringe or other device that might otherwise form a seal therewith if the stem 22 was configured circular cylindrically. Other configurations of the stem 22 may be employed without departing from the spirit and scope of this invention to preclude sealing with the tip of the access device, such as for example the slots and notches shown in the Dome Check Valves of U.S. Pat. Nos. 7,296,782 and 7,641,174 cited above.

Unlike the Dome Check Valves of U.S. Pat. Nos. 7,296,782 and 7,641,174 cited above, in the present invention the dome-shaped valve element 18 includes a plurality of equally-spaced cut-outs 26 (six are shown). The cut-outs 26 allow fluid flow therethrough thereby increasing the amount of fluid flow that may flow through the valve 10 when the valve element 18 is cracked open. The cut-outs 26 also streamline the fluid flow while minimizing the potential for air entrapment under the dome-shaped valve element 18. The generally dome-shaped configuration of the valve element 18 further comprises an integral annular skirt 30 extending about its periphery.

It is noted that the plurality of cut-outs 26 define a plurality of equally-spaced legs 28 (six are shown) extending generally radially outward then downwardly to merge into the annular skirt 30. The width of the legs 28 is defined by the width of the cut-outs 26, preferably to thereby define legs 28 having sufficient strength to achieve the desired cracking pressure (i.e., the heftier the legs 28 the studier they will be to increase the amount of cracking pressure necessary to crack the valve element 18).

Figure 6:
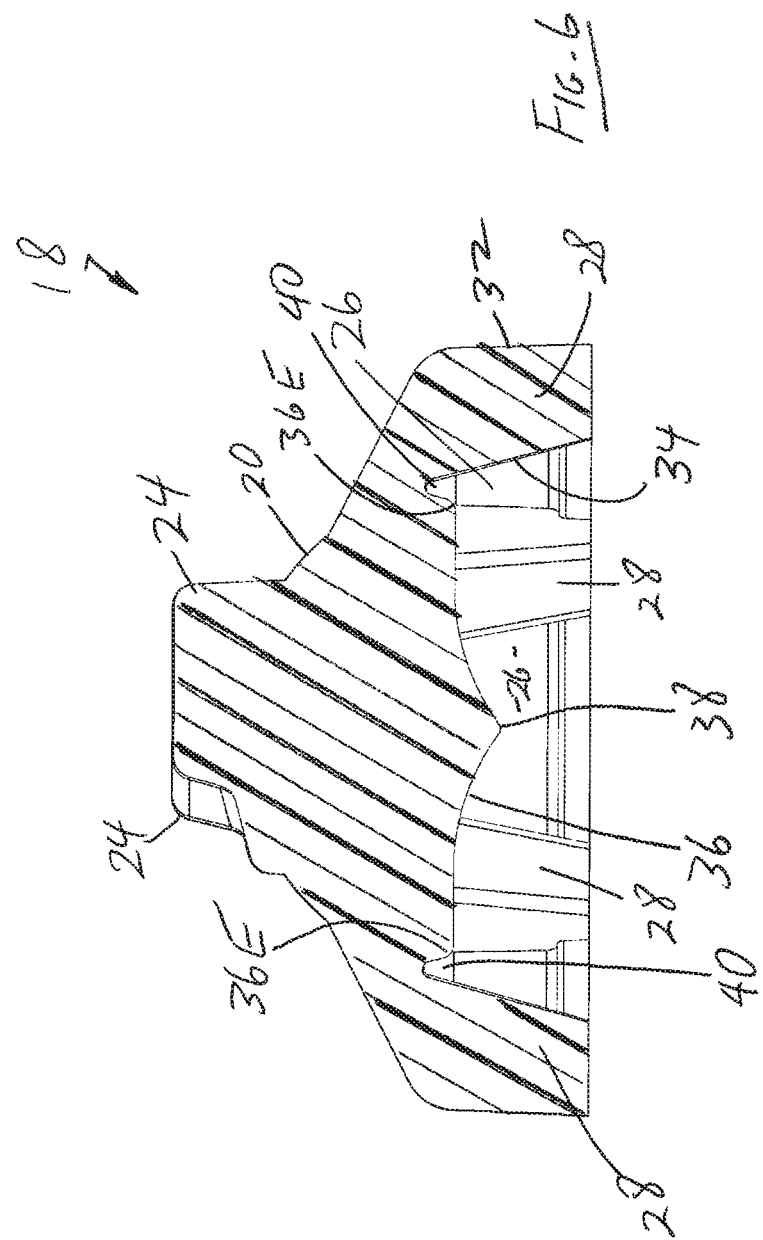
FIG. 6 is a cross-sectional view of FIG. 4 along lines 6-6.
Figure 7:
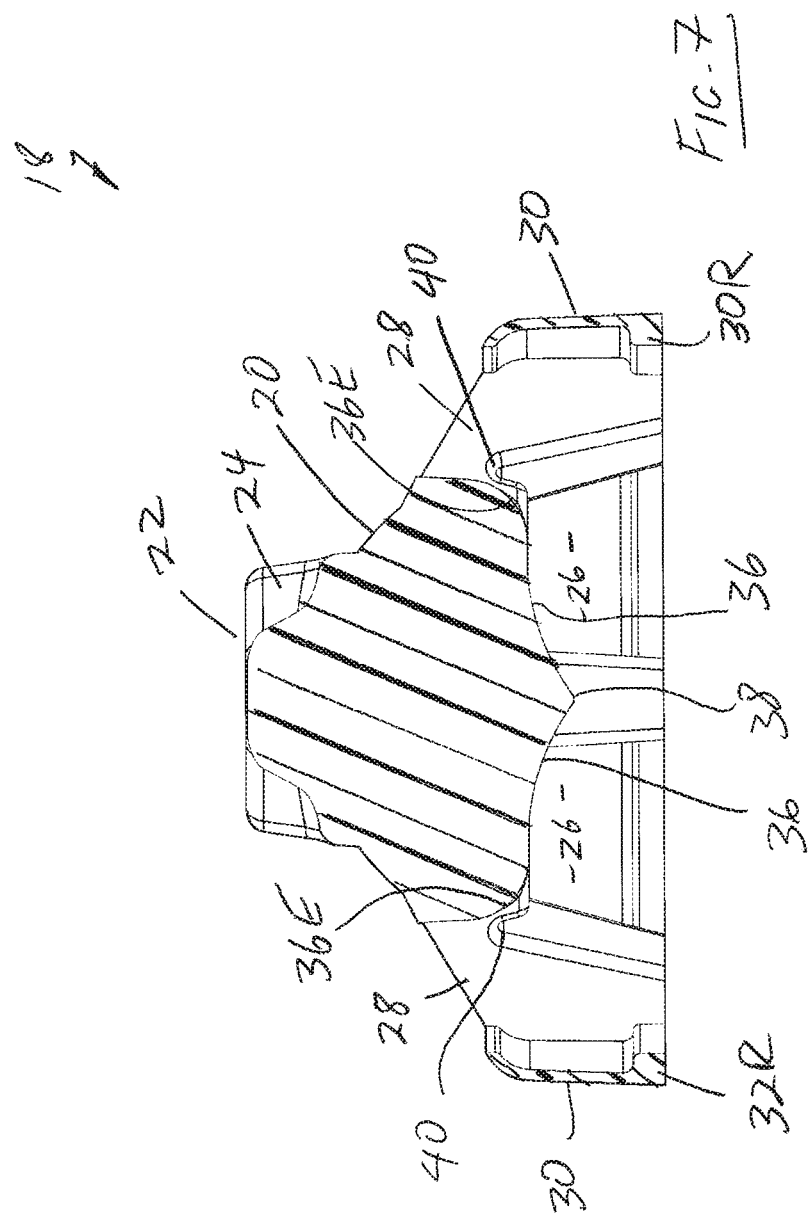
FIG. 7 is a cross-sectional view of FIG. 4 along lines 7-7.

As best shown in FIG. 6 as compared to FIG. 7, each of the legs 28 comprise an outer side wall 32 sloping outwardly from the inlet at a first angle and an inner side wall 34 sloping outwardly from the inlet at a second angle greater than the first angle, thereby achieving a substantially thick configuration. In comparison, the integral annular skirt 30 comprises a substantially thin configuration that serves to stabilize the legs 28 and keep them in their generally radial configuration relative to one another. The bottommost annular edge of the skirt 30 includes an inwardly extending rim 30R of increased thickness to provide additional stability.

FIGS. 6 and 7 further illustrate the configuration of the underside of the dome-shaped valve element 18 as including a generally concave portion 36 extending circularly annularly about the underside to define an outwardly extending point 38 in the form of an upside-down three dimensional hyperbolic curve (i.e., similar to the curve of a single pole fabric tent). The concave portion 36 precludes the entrapment of air underneath the valve element 18 that might otherwise occur with the prior art dome check valves noted above. As shown in FIG. 7, the peripheral edges 36E of the concave portion 36 are rounded to blend into the cut-outs 26 and in doing so, as shown in FIG. 6, define undercuts 40 between the peripheral edges 36E and the legs 28 while further streamlining the fluid flow through the cut-outs 26. The undercuts 40 function as a living hinge to facilitate the dome-shaped valve element 18 moving inwardly during cracking in a precise, controlled manner while further streamlining the fluid flow around the otherwise sharp corners between the legs 28 and the peripheral edges 36E.

Figure 8:
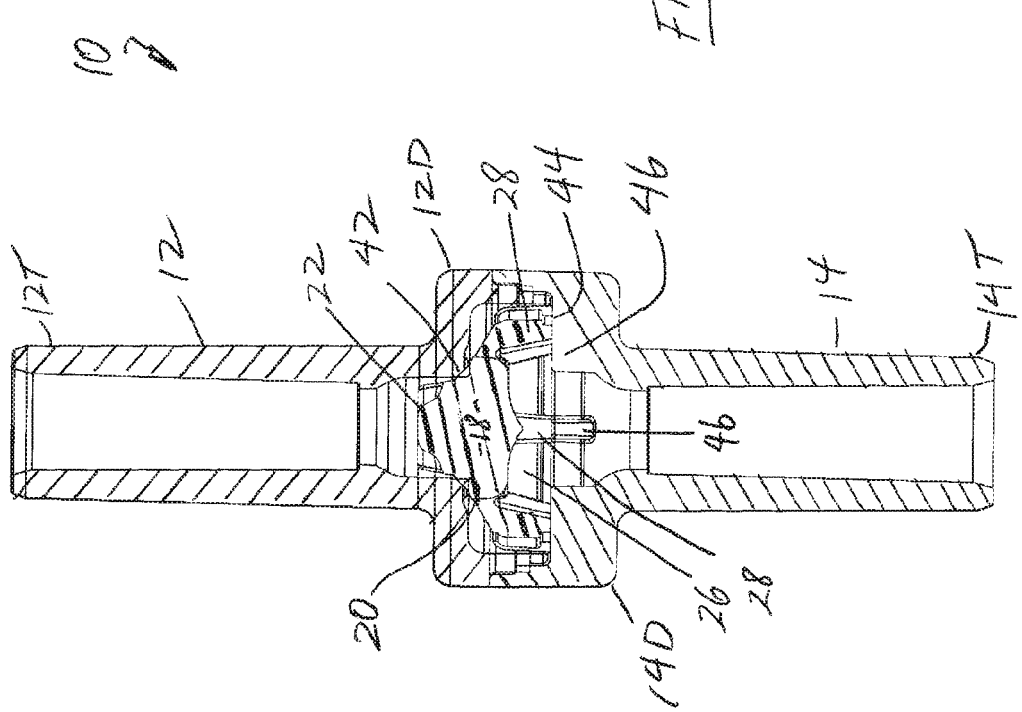
FIG. 8 is a longitudinal cross-sectional view of FIG. 1.

Referring to FIG. 8 in combination with FIGS. 2 and 3, the inside of the dome-shaped larger diameter configuration 12D of the inlet housing 12 comprises an annular valve seat 42 which forms a seal with the upper surface of the dome-shaped configuration 20 of the valve element 18 when the valve element 18 is in its at rest position within the housings 12 & 14. The inside of the dome-shaped larger-diameter configuration 14D of the outlet housing 14 comprises an annular seat 44 on which the inwardly extending rim 30R of the annular skirt 30 is seated when the valve element 18 is in its at rest position within the housings 12 & 14. The inside of the dome-shaped larger-diameter configuration 14D of the outlet housing 14 comprises a plurality of castellations 46 (four are shown) having an inside diameter that is appreciably less than the outside diameter of the hyperbolic curve defined by the concave portion 36 to limit the inward travel of the valve element 18 as it is cracked open. It is noted that the number of legs 28 versus the castellations 46 are preferably different.

In operation, at rest bidirectional fluid flow through the valve 10 is blocked by virtue of the seal formed between the annular valve seat 42 and the upper surface of the dome-shaped configuration 20 of the valve element 18 under the resilient force of the legs 28 and skirt 30. The valve 10 may be opened or "cracked" either by fluid pressure in its inlet housing 12 or by a physical object such as the tip of a syringe that exerts a force on the central integral stem 22 of the valve element 18 against the resilient force of the legs 28 and skirt 30. Once the valve element 18 is cracked opened, fluid flow from the inlet housing 12 flows around the stem 22 radially across the outer surface of the dome-shaped configuration 20 of the valve element 18, through the cut-outs 26 past the legs 28 and the castellations 46 and then out via outlet housing 14. Importantly, a substantial flow of fluid is allowed to pass through the valve 10 once the valve element 18 is cracked. Once the cracking pressure is removed, either by the lack of sufficient pressure of the incoming fluid in inlet housing 12 or by removal of the object that cracked the valve 10, the inherent resiliency of the legs 28 and skirt 30 urges the dome-shaped configuration 20 of the valve element 18 back into sealing engagement with the annular valve seat 42 of the inlet housing 12. Preferably, the sealing force caused therebetween is sufficient to assure an adequate seal even when there is no fluid pressure in the outlet housing 14. Moreover, the dome-shaped configuration 20 of the valve element 18 is capable of remaining sealed even when significant back fluid pressure exits in the outlet housing 14. Further, the limited travel of the dome-shaped configuration 20 coupled with its dome-shaped configuration 20, assures that the valve element 18 does not deform (i.e., is not blown out) even when very high pressures exist in the inlet housing 12.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described,

What is claimed is:

1. A check valve, comprising in combination:
   a housing having an inlet with a dome-shaped interior configuration and an outlet;
   an elastomeric dome-shaped valve element positioned entrained between said inlet and said outlet to form a seal against said inlet, said elastomeric dome-shaped valve element having a plurality of cut-outs that allow fluid flow therethrough thereby increasing the amount of fluid flow that may flow through the check valve when said elastomeric dome-shaped valve element is cracked open;
   said elastomeric dome-shaped valve element further comprising an integral annular skirt extending about its periphery;
   said plurality of cut-outs define a plurality of equally-spaced legs extending generally radially outward then downwardly to merge into said annular skirt;
   a width of said plurality of equally-spaced legs is defined by a width of said plurality of cut-outs to define said plurality of equally-spaced legs whose strength achieves a cracking pressure;
   an underside of said elastomeric dome-shaped valve element including a generally concave portion extending circularly annularly about said underside to define an outwardly extending point having a form of an upside-down three dimensional hyperbolic curve that precludes entrapment of air underneath said elastomeric dome-shaped valve element;
   said elastomeric dome-shaped valve element further comprising a central stem;
   said outlet comprising a dome-shaped interior configuration;
   said dome-shaped interior configuration of said inlet comprising an annular valve seat which forms a seal with an upper surface of said elastomeric dome-shaped valve element when said elastomeric dome-shaped valve element is in its at rest position within the housing;
   said dome-shaped interior configuration of said outlet comprising an annular seat on which said inwardly extending rim of said annular skirt is seated when said elastomeric dome-shaped valve element is in its at rest position; and
   a plurality of castellations having an inside diameter that is appreciably less than an outside diameter of said hyperbolic curve defined by said concave portion to limit inward travel of said elastomeric dome-shaped valve element as it is cracked open.

2. The check valve as set forth in claim 1, wherein peripheral edges of said concave portion blend into said plurality of cut-outs to define undercuts between said peripheral edges and said plurality of equally-spaced legs to function as a living hinge to facilitate said elastomeric dome-shaped valve element moving inwardly during cracking.

3. The check valve as set forth in claim 1, wherein said central stem is frustoconical and extends into said inlet.

4. The check valve as set forth in claim 1, wherein said central stem comprises a star-shaped configuration with a plurality of equally-spaced radial projections to allow fluid flow therearound.

5. The check valve as set forth in claim 1, wherein said plurality of cut-outs are equally-spaced.

6. The check valve as set forth in claim 1, wherein said plurality of equally-spaced legs each comprise an outer side wall sloping outwardly from said inlet at a first angle and an inner side wall sloping outwardly from said inlet at a second angle greater than said first angle.

7. The check valve as set forth in claim 6, wherein said integral annular skirt comprises a configuration that stabilizes said plurality of equally-spaced legs and maintains them in a generally radial configuration relative to one another.

8. The check valve as set forth in claim 7, wherein a bottommost annular edge of said integral annular skirt includes an inwardly extending rim of increased thickness to provide additional stability.

9. The check valve as set forth in claim 1, wherein a number of said plurality of equally-spaced legs is different than a number of said plurality of castellations.

10. The check valve as set forth in claim 9, wherein, at rest bidirectional fluid flow through the check valve is blocked by virtue of the seal formed between said annular valve seat and said upper surface of said elastomeric dome-shaped valve element under a resilient force of said plurality of equally-spaced legs and said annular skirt.

11. The check valve as set forth in claim 10, wherein the elastomeric dome-shaped valve may be cracked open by a physical object inserted into said inlet that exerts a force on said central stem against said resilient force of said plurality of equally-spaced legs and said annular skirt, whereupon fluid flow from said inlet flows around said central stem radially across an outer surface of said elastomeric dome-shaped valve element, through said plurality of cut-outs past said plurality of equally-spaced legs and said plurality of castellations and then exit via said outlet.

* * * * *